United States Patent [19]
Swanson

[11] Patent Number: 6,088,614
[45] Date of Patent: Jul. 11, 2000

[54] TISSUE CHARACTERIZATION TO IDENTIFY AN ABLATION SITE

[75] Inventor: David K. Swanson, Mountain View, Calif.

[73] Assignee: Boston Scientific Corporation, Natick, Mass.

[21] Appl. No.: 08/832,608

[22] Filed: Mar. 31, 1997

[51] Int. Cl.$^7$ ........................................ A61B 5/04
[52] U.S. Cl. ............................ 600/510; 606/41; 600/374
[58] Field of Search .................................. 600/373–375, 600/509, 510, 515, 518; 606/41; 607/122, 98, 101

[56] References Cited

U.S. PATENT DOCUMENTS

| | | | |
|---|---|---|---|
| 5,546,940 | 8/1996 | Panescu et al. | 128/642 |
| 5,577,509 | 11/1996 | Panescu et al. | 128/696 |
| 5,582,609 | 12/1996 | Swanson et al. | 606/39 |
| 5,595,183 | 1/1997 | Swanson et al. | 128/697 |
| 5,598,848 | 2/1997 | Swanson et al. | 128/696 |
| 5,601,088 | 2/1997 | Swanson et al. | 128/697 |

OTHER PUBLICATIONS

"Entrainment Techniques for Mapping Atrial and Ventricular Tachycardias", by Stevenson et al., Journal of Cardiovascular Electrophysiology, vol. 6, pp. 201–216, Mar. 1995.
"Identification Of Reentry Circuit Sites During Catheter Mapping And Radiofrequency Ablation Of Ventricular Tachycardia Late After Myocardial Infaction", by Stevenson et al., Circulation from the Divisions of Cardiology, UCLA School of Medicine, vol. 88, No. 4, Part 1, Oct. 1993.
"Radiofrequency Catheter Ablation of Ectopic Atrial Tachycardia Using Paced Activation Sequence Mapping", by Tracy et al., Journal of the American College of Cardiology, vol. 21, No. 4, Mar. 15, 1993, pp. 910–917.
"Catheter Ablation of Ventricular Tachycardia Related to Coronary Heart Disease", by Dubec et al, Hopital du Sacre Coer de Montreal and Department of Medicine, and Institut de Genie Biomedical, vol. 87, No. 2, Feb. 1993, pp. 649–651.
"Endocardial Activation Mapping and Endocardial Pace–Mapping Using a Balloon Apparatus", by Fann et al., The American Journal of Cardiology, vol. 55, Apr. 1, 1995, pp. 1076–1083.
"Holter Triage Ambulatory ECG Analysis", Cooper et al., Journal of Electrocaridology, vol. 29, No. 1, Jan. 1996, pp. 33–38.
IEEE Transactions on Biomedical Engineering, vol. 42, No, 7, Jul. 1995, "On the Detection of QRS Variations in the ECG", by Shaw et al., pp. 736–741.

*Primary Examiner*—Jeffrey R. Jastrzab
*Attorney, Agent, or Firm*—Lyon & Lyon LLP

[57] ABSTRACT

Heart tissue near the surface of the heart is characterized to identify a potential site to ablate to treat reentrant ventricular tachycardia. Signals from the surface of the heart are recorded during an episode of ventricular tachycardia to determine whether a reentrant pathway lies near the surface of the heart. Entrainment pacing is employed to identify a potential ablation site near the slow conduction zone of the reentrant pathway. Heart tissue is ablated by creating a lesion with a large surface area and a shallow depth to destroy the slow conduction zone.

25 Claims, 5 Drawing Sheets

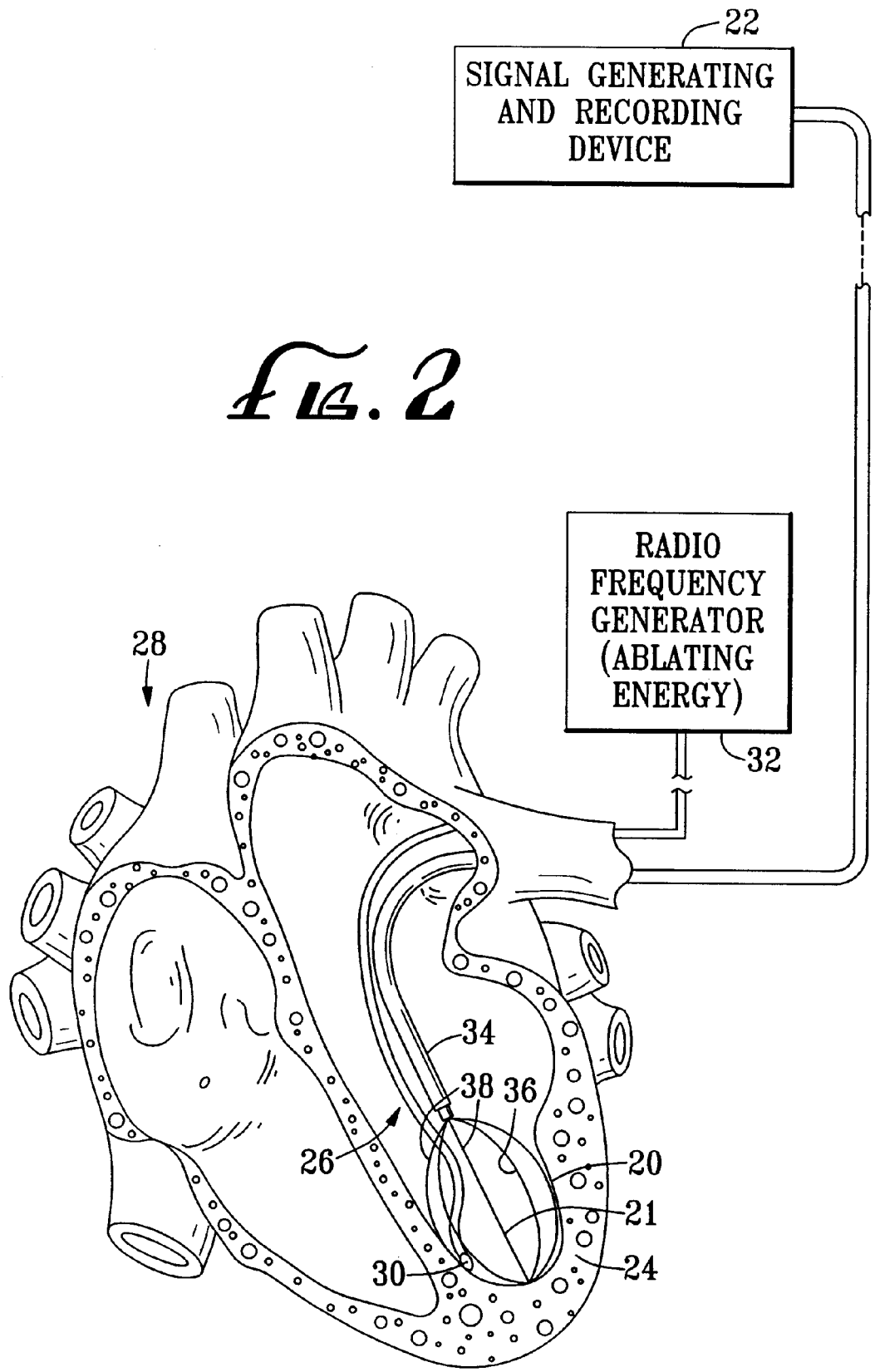

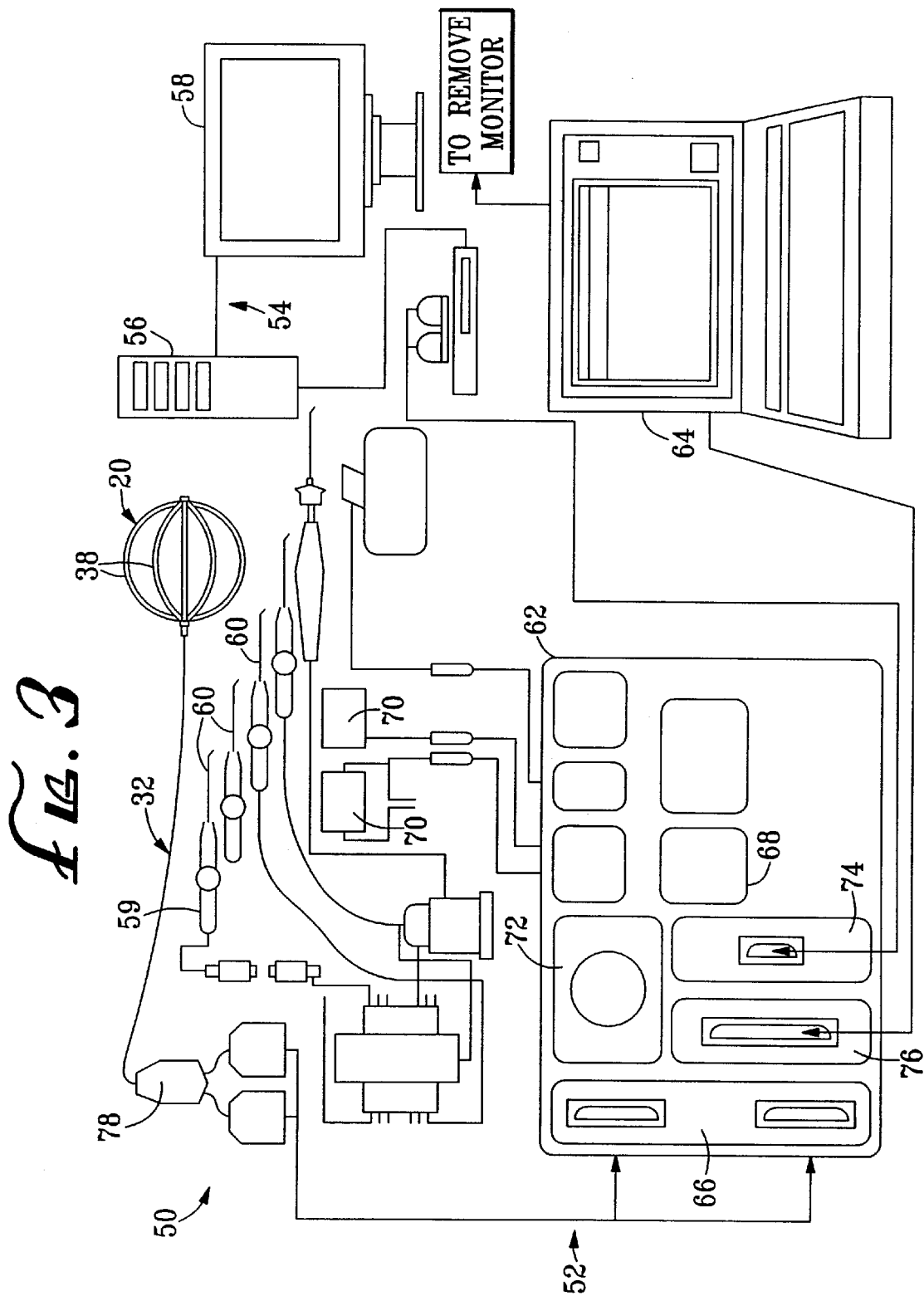

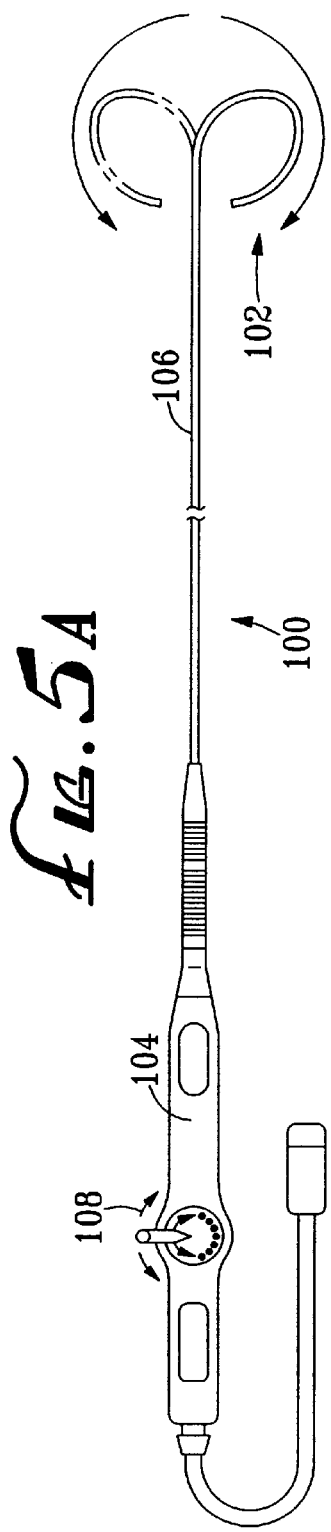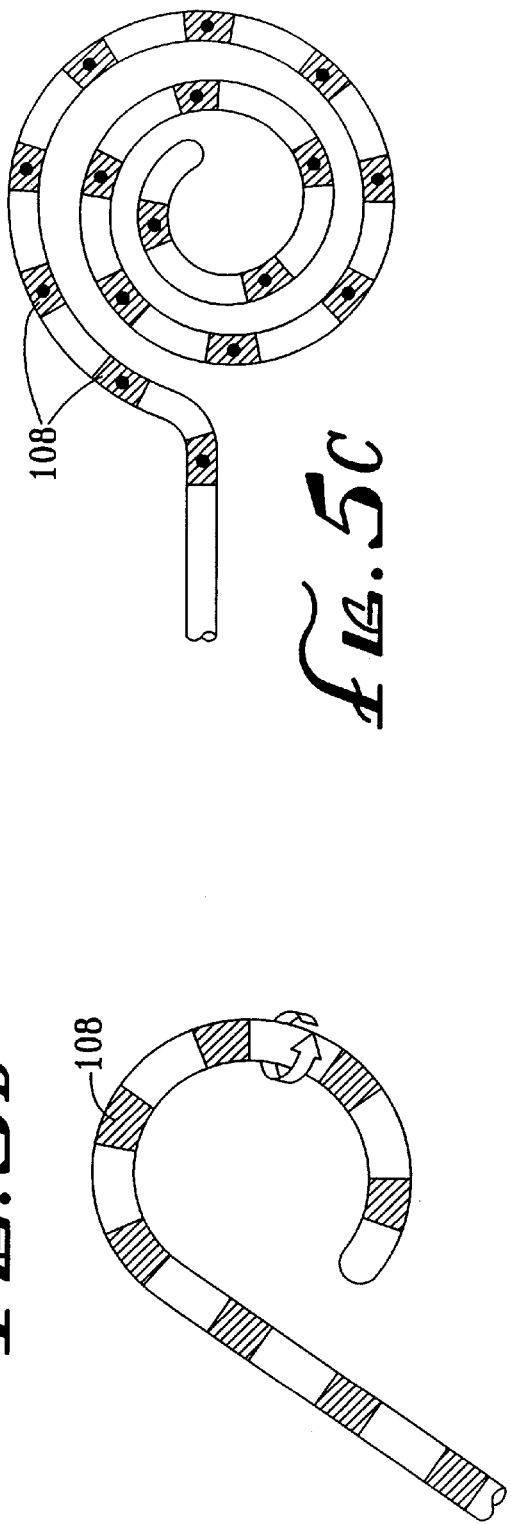

TISSUE CHARACTERIZATION TO IDENTIFY AN ABLATION SITE

TECHNICAL FIELD

This invention relates to characterizing tissue and, more specifically to characterizing tissue on a surface of a heart to determine potential ablation sites to treat ventricular tachycardia.

BACKGROUND INFORMATION

A normal heartbeat involves generation of an electrical impulse and propagation of the electrical impulse across the heart, which causes each chamber of the heart to appropriately contract. Sometimes aberrant conductive pathways develop in heart tissues, and these disrupt the normal path of the electrical impulse. For example, anatomical obstacles or conduction blocks in heart tissue can disrupt the normal propagation of an impulse by causing the impulse to degenerate into several circular wavelets that circulate about the obstacles, thus disrupting normal activation within the heart tissue and chambers. Slow conduction zones in animal and human hearts constrained by anatomical or conduction blocks are believed to exist. Such a zone is a localized region of the heart tissue which propagates an impulse at a slower speed than normal heart tissue thus sometimes resulting in errant, circular propagation patterns or reentrant pathways. Reentrant pathways provide the substrates for the re-excitation of a region of cardiac tissue by an excitatory wavefront, reentry may continue for one or more cycles and sometimes result in tachycardia. Reentrant ventricular tachycardia (VT) is an abnormally rapid ventricular rhythm with aberrant ventricular excitation (wide QRS complexes), usually in excess of 150 per minute, which is generated within the ventricle of the heart as a result of a reentrant pathway.

To treat VT, it is desirable first to determine the physical location of the aberrant pathways. Once located, the heart tissue in the pathway can be destroyed in a process termed ablation by heat, chemicals, and/or other means. Heat can be generated in the targeted tissue using, for example, RF, microwave, ultrasonic, or lasers to effect the ablation lesion. Ablation can remove the aberrant conductive pathway, restoring normal myocardial contraction. More specifically, to treat VT, the slow conduction zone must be located and destroyed or partially destroyed, with the goal of eliminating the slow conduction zone's ability to conduct electrical impulses.

Existing ablation techniques for treating VT tend to focus on creating large lesions to ensure a high cure rate. In fact, companies that produce ablation apparatus compete to produce ablation electrodes that create larger volume lesions. For example, a chilled ablation tip electrode produces a larger lesion than a conventionally-sized ablation tip. Other technologies being pursued to produce larger ablation lesions include using microwave catheters, laser catheters, and chemical ablation.

Tissue ablation for treating VT, however, involves a trade-off. The trade-off is between the need to produce a large enough lesion to ensure a high cure rate and the need to limit the destruction of other viable heart tissue. In certain situations, large surface area lesions that are not very deep may be preferred. For example, if the slow conduction zone is located near the endocardial surface of the heart, creation of a shallow lesion having a large surface area is preferred over a deep lesion. An ablation method for creating a shallow lesion by itself, however, is not completely helpful if it fails to teach how one determines when only a shallow lesion is necessary. Without this determination, one would have to create lesions as part of a trial and error approach. The trial and error method, however, is harmful to a patient since many lesions may be placed at incorrect locations, unnecessarily destroying viable heart tissue. Therefore, what would be helpful, and what is lacking, is a way of determining that only a shallow region is required.

SUMMARY OF THE INVENTION

The invention relates to characterizing tissue. More specifically, it relates to characterizing heart tissue to determine whether creating a shallow lesion at the tissue site by ablation could treat reentrant VT.

In accordance with the invention, the heart is first analyzed to determine whether a reentrant pathway lies near a surface of the heart. The analysis involves recording signals from a surface of the heart during an episode of VT and evaluating the recorded signals to find diastolic or pre-systolic potentials. If the reentrant pathway is determined to lie near a surface of the heart, tissue on the surface of the heart is assessed to determine if it is near a critical zone (i.e., the slow conduction zone) of the reentrant pathway. The assessment involves using entrainment pacing on the tissue on the heart surface. The entrainment pacing procedure involves applying a pacing signal to heart tissue to stimulate the tissue, and then analyzing a post-pacing response signal. If the tissue is determined to be near the critical zone of the reentrant pathway, the tissue is ablated to create a lesion that has a shallow depth but a large surface area.

The invention also relates to a system for characterizing heart tissue to identify a potential ablation site to treat VT. The system includes at least one electrode and a signal generating and recording device. A single roving electrode can be used, or multiple electrodes. The electrodes are adapted for receiving signals from a surface of the heart during an episode of VT. The electrodes also are adapted for applying signals to and receiving signals from the heart during an entrainment pacing procedure. The signal generating and recording device is connected to the electrodes. The signal generating and recording device is able to display diastolic or pre-systolic potentials during an episode of VT, if a reentrant pathway is located near the electrodes. The signal generating and recording device also is able to generate pacing signals and display post-pacing intervals during an entrainment pacing procedure.

In one aspect, the invention relates to a method for characterizing heart tissue. The method comprises recording signals from a surface of the heart during an episode of ventricular tachycardia and determining whether a reentrant pathway lies near the surface of the heart.

In embodiments of this aspect of the invention, the method can further comprise assessing whether tissue of the heart is near a slow conduction zone of the reentrant pathway. This assessing step can include entrainment pacing the heart tissue. The step of entrainment pacing can comprise applying a pacing signal to the heart tissue and analyzing a post-pacing signal. This applying step can comprise applying the pacing signal which is in the range of about 1 milliAmpere to about 10 milliAmperes. The applying step can further comprise applying the pacing signal to the heart tissue to stimulate the heart tissue, and the analyzing step can comprise analyzing the post-pacing signal to measure a time interval from when the heart tissue is stimulated to a time when depolarization of the heart tissue is evident on surface ECG leads. The method also can further comprise ablating the heart tissue to create a shallow lesion if the heart tissue is near the slow conduction zone of the reentrant pathway. This ablating step can comprise ablating the heart tissue to create the shallow lesion with a large surface area. The ablating step also can comprise ablating the heart tissue to create the shallow lesion having a depth in the range of about 3 millimeters to about 4 millimeters. The ablating step can comprise using a multiple electrode ablation catheter to ablate the heart tissue to create the shallow lesion or using a balloon ablation catheter to ablate the heart tissue to create the shallow lesion.

In other embodiments of this aspect of the invention, the method can include recording by placing one or more electrodes on the surface of the heart to record signals from the surface of the heart. The recording step can include recording signals from an endocardial surface of the heart. The recorded signals can be evaluated to find diastolic or pre-systolic potentials.

In another aspect, the invention involves a system for characterizing heart tissue to identify an ablation site. The system includes at least one electrode for monitoring and stimulating the heart, for receiving signals from a surface of the heart during an episode of ventricular tachycardia, and for applying and receiving signals to and from the heart during an entrainment pacing procedure. The system also includes a signal generating and recording device, coupled to the at least one electrode, for displaying diastolic or pre-systolic potentials during the episode of ventricular tachycardia when a reentrant pathway is located near the at least one electrode and for producing a pacing signal and displaying a post-pacing signal during the entrainment pacing procedure.

Embodiments of this aspect of the invention can include the following features. For example, the system can further comprise a multiple electrode catheter which includes the at least one electrode, such as a basket catheter. Alternatively, a roving catheter can be used. The signal generating and recording device can includes a computer-controlled electrogram recording and stimulating system capable of controlling pacing pulse parameters, pacing intervals, and a sequence of electrode sites at which pacing signals are applied. The system can further include a source of ablation energy (e.g., a radio frequency generator) and an ablation catheter coupled to the source of ablation energy for controllably producing a lesion having a large surface area and a shallow depth. The ablation catheter can be, for example, a balloon ablation catheter or a multiple electrode ablation catheter.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2 is a schematic diagram of a system which embodies features of the invention.

FIG. 3 is a simplified diagram of a signal generating and recording device.

FIG. 5A is a schematic diagram of a multiple electrode ablation catheter.

FIG. 5B is a diagram of one embodiment of the energy emitting region of the multiple electrode ablation catheter of FIG. 5A.

FIG. 5C is a diagram of one embodiment of the energy emitting region of the multiple electrode ablation catheter of FIG. 5A.

DESCRIPTION

In the heart of a person suffering from VT, the slow portions of the heart having a reentrant pathway that sustain VT include a relatively small volume of tissue. Thus, electrical activity from the tissue in the slow zone cannot be seen from electrodes located on the skin of a person or an animal. Even if the electrodes are inside near the heart, the electrodes may not be able to detect signals from these regions. Research studies in both humans and animals show that diastolic potentials that can be recorded on the endocardium of the heart are not able to be recorded from electrodes on the epicardium of the heart, and conversely, diastolic potentials from slow conduction zone near the epicardium of the heart that may be recorded from epicardial electrodes can not be recorded from endocardial electrodes. With certain arrhythmias, diastolic potentials that are separated in time from one another are recorded from both epicardial and endocardial sites. However, this is a situation in which the reentrant pathway of the slow conduction zone includes both subendocardial and subepicardial tissues and by inference mid-myocardial tissue. Therefore, electrodes must be located close to the slow conduction zone in order to record potentials from the slow conduction zone.

Figure 1:
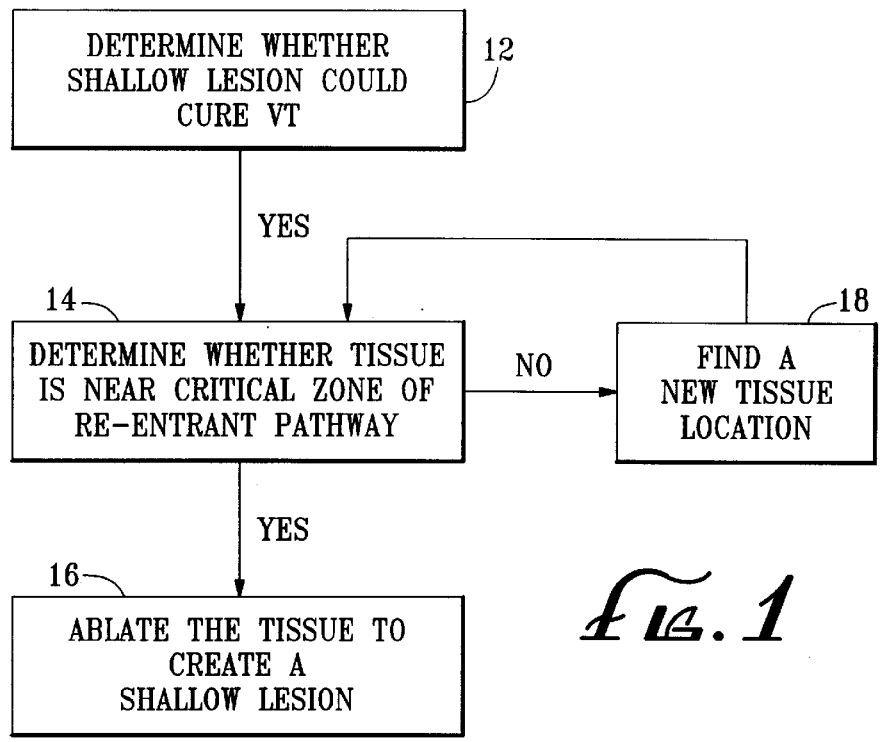
FIG. 1 is a flow chart of a method for characterizing heart tissue according to the invention.

The present invention takes advantage of this requirement in evaluating a heart that requires a treatment for VT. Referring to FIG. 1, according to the invention, a determination is made as to whether the slow conduction zone is situated near the endocardial surface of the heart before heart tissue is destroyed by ablation (step 12). A slow conduction zone located near a surface of the heart can be destroyed by ablation which creates a shallow lesion. The determination requires recording signals from the endocardial surface of the heart during an episode of VT by placing multiple electrodes or at least one roving electrode on the endocardial surface, substantially covering all of the surface. If diastolic or pre-systolic potentials are not observed on the endocardial surface during VT, the slow conduction zone is not located near the endocardial surface. Therefore, ablation that creates a shallow lesion would not treat the VT. If, however, diastolic or pre-systolic potentials are observed from the electrodes located on the endocardial surface, the slow conduction zone is likely to be located near the surface of the endocardial zone. Such potentials establish that tissue near the recording electrodes is activated by the reentrant pathway of the slow conduction zone and that tissue cannot directly activate the mass of the more normal myocardium. In most cases of reentrant VT, diastolic or pre-systolic potentials are observed from endocardial electrodes. In these circumstances, ablation that creates a shallow lesion could treat VT.

Identifying diastolic or pre-systolic potentials does not, however, indicate which area on the endocardial surface of the heart needs to be ablated. This is because the identified potentials do not establish that the recording electrodes are near the critical zone or the slow conduction zone of the reentrant pathway. The electrodes may be recording from a bystander site.

According to the invention, selected locations on the endocardial surface of the heart are entrainment paced to find tissue near the critical zone of the reentrant pathway (step 14 of FIG. 1). A pacing signal having an amplitude between 1 milliAmpere (mA) to 10 mA is applied through a selected electrode to stimulate the tissue around the electrode. A signal with this amplitude stimulates tissue within 1 millimeter (mm) to 2 mm from the electrode. An analysis of the post-pacing signal shows whether the stimulated tissue is near the slow conduction zone or is a bystander site.

If the stimulated tissue is found to be a bystander site, entrainment pacing is repeated with another electrode to stimulate another tissue area (step 18). On the other hand, if the stimulated tissue is found to be near the slow conduction zone, the tissue is ablated creating a shallow lesion to destroy the slow conduction zone (step 16). The term "shallow lesion" refers to a lesion that has a depth of approximately 3 mm to 4 mm.

Although the method for characterizing tissue is described in FIG. 1 with respect to endocardium of the heart, the method applies equally to tissue on the epicardial surface of the heart. Mapping and ablating an epicardial surface of the heart is achieved through thorascopic techniques or thoracotomy.

The system for characterizing tissue as described in FIG. 1 includes at least one electrode, a signal generating and recording device, an ablation catheter, and a source of ablation energy. The electrode or electrodes record signals from the endocardial surface of the heart during an episode of VT. The electrode or electrodes also apply pacing signals to suspected tissue sites and receive response signals during entrainment pacing. The signal generating and recording device processes signals from the heart and displays these signals for tissue characterization. The ablation catheter is capable of controllably ablating a tissue to create a lesion having a large surface area and a shallow depth. The ablation catheter is connected to a source of ablation energy. In one embodiment, the ablation catheter and the catheter including electrodes for applying and recording signal to and from the heart may be the same catheter.

Referring to FIG. 2, multiple electrodes 38 connected to a signal generating and recording device 22 are in contact with a large portion of an endocardial surface 24 of the left ventricle 26 of a heart 28. An ablation catheter 30 connected to a radio frequency (RF) generator 32 is in contact with a selected location on the endocardial surface 24.

The electrodes used with the present invention are any electrodes capable of sending and receiving electrical signals and being placed in a heart chamber. In one embodiment, a basket catheter described in U.S. Pat. No. 5,577,509 (which is incorporated in its entirety by reference) is deployed with minimal invasion in a ventricle of the heart. Referring to FIG. 2, a basket catheter 20 comprises a flexible catheter tube 34 which carries a multiple-electrode support assembly 21. The multiple-electrode support assembly 21 comprises an array of flexible spline elements 36 assembled to form a three dimensional basket structure. The support assembly 21 retains the spline elements 36 in a circumferentially spaced array. The circumferentially spaced spline elements 36 make contact with a circumferentially spaced region of a heart chamber 26. The spline elements 36 carry an array of electrodes 38 for contacting the endocardial surface. In a preferred embodiment, the electrodes 38 are made of platinum or gold-plated stainless steel bands affixed to only one side of the spline elements 36. This is the side of the spline elements 36 that, in use, contacts endocardial tissue. The opposite surface of the spline elements 36 is free of electrodes 38.

In another embodiment, a roving electrode is used to sense signals from multiple locations on the endocardial surface of the heart chamber by moving to a different location after completing a measurement from one site. The roving electrode is likewise moved around to apply pacing signals to different locations of the heart.

Referring to FIG. 3, a basket catheter 20 is connected to a signal generating and recording device 50. In general, the signal generating and recording device 50 can be used to perform all of the generation, determination, assessment, analysis, processing, etc. described herein. The device 50 includes an interfacing system 52 and a recorder system 54. The recorder system 54 includes a recording/processing unit 56 and a display unit 58 to record, store, analyze and display signals acquired by the multiple electrodes 38 and other catheters 59 with electrodes 60, if there are any. The interfacing system 52 couples the multiple electrodes 38 to the recorder system 54 via an interface unit 62, enabling information acquired by the multiple electrodes 38 to be loaded into the recorder system 54. The interface unit 62 is coupled to a laptop computer 64. The interface unit 62 operates under the command of the laptop 64 to interconnect the electrodes 38 to the recorder system 54. The laptop 64 responds to requests and instructions entered onto its keyboard by an operator to switch among the electrodes as required to achieve a desired function. The interface unit 62 has multiple input and output ports for connection to external devices. Port 66 is provided for connection to the catheter 32. Port 68 is provided for connection to external pacing pulse generator or stimulator 70. Pacing pulses generated by the external pacing pulse generator 70 can be selectively coupled to any of the electrodes 38. Port 72 permits connection to additional catheters 59. Port 74 provides for connection to the recorder system 54, and port 76 provides for connection to the laptop 64. The signal generating and recording device 50 also is described in pending U.S. patent application Ser. No. 08/770,971 which was filed on Dec. 20, 1996, which description is hereby incorporated by reference.

In one embodiment, an operator manually inputs pacing signal parameters including pacing cycle interval and the sequence of electrode locations at which the pacing signals are applied into the signal generator 70. In another embodiment, the electrodes 38 are connected to a switching element 78. The switching element 78 enables automated (e.g., computer) control of the pacing signal parameters, pacing cycle interval, and the sequence of electrode locations at which the pacing signals are applied. In a preferred embodiment, the signal generator 70 enables the operator to pace the heart from one of the electrodes 38, using either operator input or a computer algorithm selected by the operator. In a preferred embodiment, the signal has the capability to pace from each electrode of the multiple electrodes 38 in any sequential order. In addition, the signal generator 50 can pace the heart at a predetermined constant rate or at variable rates.

The heart is monitored during an episode of VT and also during entrainment pacing. To monitor the heart, at least some of the electrodes 38 and preferably most of the electrodes 38 are connected to the signal recording device 50.

In one embodiment, all of the multiple electrodes 38 of the basket catheter 20 are connected to the signal recording unit 50 to enable continuous recording from each electrode during an episode of VT and during entrainment pacing. In another embodiment, only the electrodes not used in applying the pacing signals are connected to the recording unit 50 and used for monitoring during entrainment pacing. In a preferred embodiment, the recording unit 50 enables both unipolar recordings for any selected individual electrode and bipolar recordings for an electrode pair. In one embodiment, each electrogram complex which represents a response signal is automatically detected on all selected recording channels. The widths or duration of each electrogram complex also is automatically determined. In another embodiment, the system provides a review mode, within which the operator can edit many of the automated processing results, including electrogram detection and the time location of the leading and trailing edges of electrogram complexes.

After the electrodes 38 are placed in a selected chamber 26 of the heart 28 and appropriately connected to a signal generator and recording device 22, 50, an automated procedure that determines which electrodes 38 are in good electrical contact with the endocardium surface 24 may be initiated. Such an automated procedure is described in U.S. Pat. No. 5,598,848 which is incorporated in its entirety by reference. In one embodiment, electrical signals that activate the myocardium are emitted from one or more of the electrodes 38 and the resulting electrograms are detected to determine proper contact. The electrodes that are found to be in good electrical contact with the myocardium may be used to apply the pacing signals. Myocardium is the contractile tissue of the heart wall, more commonly called cardiac muscle.

Once an electrode or electrodes are properly placed on the endocardial surface of the heart and connected to a signal recording device, signals from the endocardial surface of the heart are recorded during an episode of VT as discussed with respect to FIG. 1. The recorded signals are analyzed to find diastolic or pre-systolic potentials. If it is determined that the slow conduction zone is likely to lie near the endocardial surface of the heart, entrainment pacing is performed using the electrodes 38 to locate tissue near the slow conduction zone.

Figure 4A:
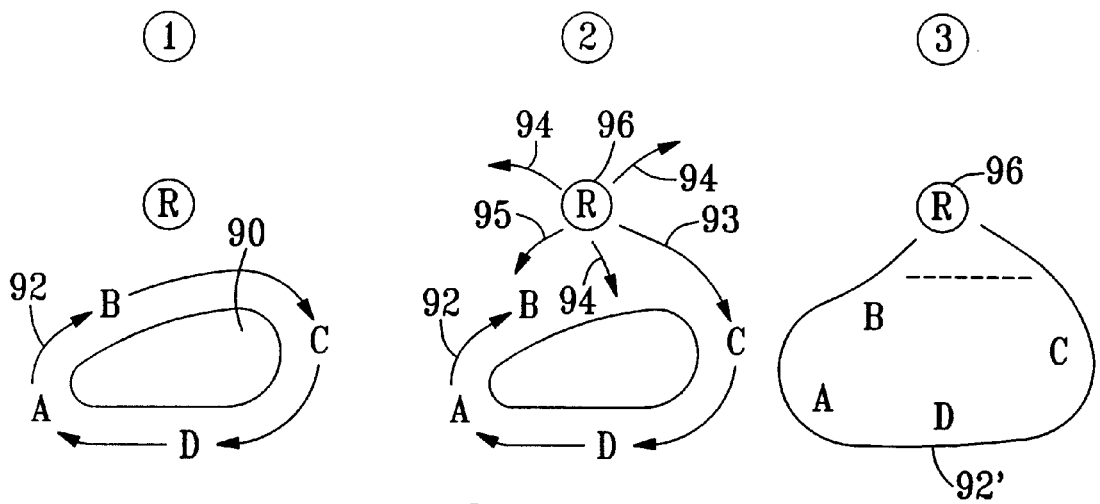
FIG. 4A is a diagram illustrating entrainment pacing at a site remote from the slow conduction zone.

Entrainment pacing assesses functional participation of a tissue site in the reentrant pathway of the slow conduction zone. Entrainment involves continuous resetting of the reentrant pathway by stimulating and capturing tissue in the pathway. Tachycardia, or fast beating of the heart, can be entrained in this manner if the tachycardia is caused by a reentrant pathway. FIG. 4A illustrates this concept. Panel 1 shows a hypothetical slow conduction zone 90 and a reentrant pathway around the slow conduction zone 92. Panels 2 and 3 show the effects of a single stimulus at site R. Site R is remote from the reentrant pathway 92. The stimulus captures and excitation waves propagate out in all directions 94 from the stimulus site R 96. The wavefronts traveling from the stimulus site R 96 to site B 95 travels in a direction opposite to the wavefronts in the reentrant pathway 92. These wavefronts 95 from site R 96 are called antidromic wavefronts. Site B is depolarized by the antidromic wavefronts 95. The wavefronts from site R traveling to site C 93 travels in the same direction as the wavefronts in the reentrant pathway 92. The wavefronts 93 traveling to site C are called orthodromic wavefronts. Site C is depolarized by the premature orthodromic wavefronts. An electrogram recorded from this site retains a similar morphology to the electrograms recorded during tachycardia. Panel 3 shows that a new reentrant pathway 92' includes site R 96.

Figure 4B:
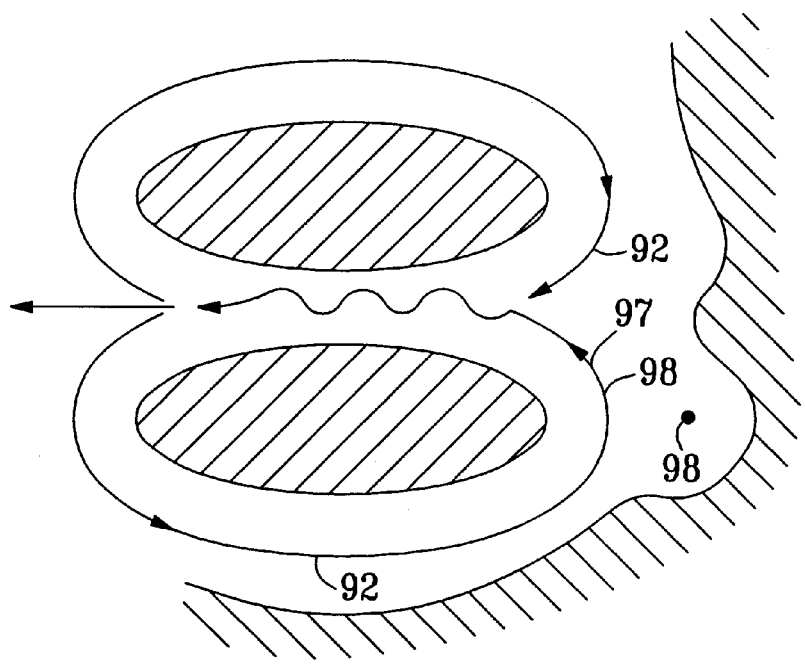
FIG. 4B is a diagram illustrating entrainment pacing at a site within the slow conduction zone.

The post-pacing interval must be analyzed to determine whether a tissue site is near the slow conduction zone or in the reentrant pathway. The post-pacing interval is the interval from the time when a tissue site is stimulated to the time when the next nonstimulated depolarization following the stimulus is measured. At the pacing site FIG. 4B shows a two-loop reentrant pathway. Referring to FIG. 4B, if a site 98 in the reentrant pathway 92 is paced the depolarization following the stimulus is the stimulated orthodromic wavefront 97 after it has propagated through the pathway 92, and returned back to the pacing site 98. This is the revolution time through the pathway 92 and equals the tachycardia cycle length. Referring to FIG. 4B, if a site 96 remote from the reentrant pathway 92 (site R) is paced, the post-pacing interval is the conduction time from the stimulus site 96 to the reentrant pathway 92, through the pathway and back to the pacing site 96. Thus, the post-pacing interval exceeds the tachycardia cycle length when a site outside the reentrant pathway is entrained. A minimum difference between the post-pacing interval and tachycardia cycle length of 30 milliseconds or less is associated with an increased likelihood that the ablation at the site will interrupt the tachycardia. Entrainment pacing is described in "Entrainment Techniques for Mapping Atrial and VTs," Stevenson et al., *J Cardiovasc Electrophysiol*, Vol. 6, pp. 201–216, March 1995.

Both automatic and manual determinations of post-pacing intervals require the identification of the electrogram complexes in each recording channel before measuring or estimating response signal interval. Automatic detection of biological signal complexes with short durations and fast repetition rates has been studied and reported in both scientific publications and in patent disclosures. Also, signal processing of electrograms including ECGs (electrocardiograms), EEGs, and other biological signals generally is well-known. Two publications describing automatic detection of the ECG waveform are: (1) "Holter triage ambulatory ECG analysis: Accuracy and time efficiency," Cooper et al., *J Electrocardiol.*, 1(1), pp. 33–38, 1996; and (2) "On the detection of QRS variations in the ECG," Shaw et al., *IEEE Trans BiomedEng.*, 42(7), pp. 736–741, 1995.

In general, all electrogram complexes have multiple peaks and zero crossings. A duration of a signal or an electrogram is defined herein to mean the time from the first "significant" deviation from the recording baseline to time at which no further "significant" deviation is observed. This definition of electrogram duration results in a non-stationary value for duration as noise is added to the system. That is, the duration becomes shorter as the signal is corrupted by more noise. For normal electrogram recordings, noise is small compared to the electrogram signal, resulting in duration determinations very close to those that would be obtained in a noise-free environment. For fractionated electrograms which are likely to result from a slow conduction zone, however, noise is significant. Therefore, signals with as low a noise level as possible is sought, and signal processing is applied to reduce the effects of noise in accordance with the invention.

Signal processing can improve the accuracy of the duration measurement. In one embodiment, where the heart is stimulated multiple times under the same condition, ensemble averaging is used to improve the effective signal-to-noise ratio. For example, if the heart is paced four times, fiducial points (i.e., identifiable features in a complex that are used as time references) for four complexes from each recording can be aligned and used to ensemble average four beats from each channel, thereby increasing the signal-to-noise level by a factor of two in each channel.

According to the invention, a more accurate electrogram duration can be determined by processing the response signals. The response signals are first converted into positive values by applying, for example, a squaring or an absolute value function. A filter then is applied to the converted signals. In one embodiment, a median filter is applied to the resulting signals. With a median filter, the boxcar width is less than half the width of the narrowest expected electrogram. In a preferred embodiment, the width is between 10 ms and 20 ms. Applying a median filter greatly distorts the shape of the waveform of the electrogram, but leaves the width of the electrogram unmodified, provided that certain conditions are met. The most important of these conditions is that the magnitude of the signal level in the complex must be well above noise level more than half the time for all time intervals equal to the boxcar width. All signals with values above a threshold level are considered significant and become a part of an electrogram complex. One method of finding the beginning and end of the complex is to search backward and forward from the peak of the processed signal to find the first occurrences of signals below the threshold to find the beginning and end of the complex, respectively.

The threshold can be defined in various ways. In one embodiment, the threshold is defined in terms of percentage of the peak electrogram amplitude. In another embodiment, the threshold is defined as a fixed signal amplitude, such as 0.1 millivolt (mV). In a preferred embodiment, the threshold is defined as a value based on characteristics of the signal being recorded, i.e., an adaptive threshold. An adaptive threshold value may be the median value of all processed signal values that are not within the electrogram complex. If the electrogram duration is less than about 25% of the pacing cycle length, the median value for all processed signal values is commonly nearly the same as the median value of all non-complex processed signals. In this usual case, the median value for all processed signal values can be used for the threshold. This is the case since in normal tissue, most signals are near the iso-electric line, i.e., the signals are very small. In the above-described method, it is valuable to process the signal values for each heart beat separately, using signal segments from 1 to 1½ cycle lengths long. Signal segments including more than one complete cycle reduces the probability that the signal segment will begin or end in the middle of an electrogram complex. When relatively short signal segments are used for analysis (e.g. 1 to 1½ cycle lengths long), sorting the processed signal values in amplitude order, while maintaining pointers to the time location for each signal value, provides a simple means to implement the above-described method for determining electrogram duration. First, choose the median of the entire processed signal segment as the initial threshold. Then, use the time location of the largest signal to begin a forward and backward search in the processed signal for the beginning and end of the complex. If the complex duration is less than ¼ the cycle length, then stop. If the width of the complex is greater than ¼ the cycle length, redefine the threshold as the median of non-complex values and repeat the search. For longer complex durations, this iteration need not be done more than two to three times, since the solution rapidly converges. For each iteration step, the new threshold can be read directly from the original sorted file, since by definition, all values in the complex were above the original value for the threshold. In addition, if the beginning and ending locations were saved, the search for the newly-defined beginning and end of the complex can begin at the saved locations. Each iteration results in an increase or no change in measured electrogram duration. The iteration terminates when no change in duration occurs. Other methods for defining the threshold value to determine the electrogram complex duration can be employed.

In another embodiment, the converted signals are processed with a low-pass filter. Low-pass filtering provides several benefits. This filtering process tends to decrease the effects of noise and removes near-zero values. The median filter is relatively tolerant to such low values. Electrogram durations will be biased to lower numbers without the low-pass filters. Also, if the median filter is chosen to be quite narrow, e.g. 5 ms, electrogram duration can be measured to be much shorter than it would be if measured manually by an expert electrophysiologist. Conventional low-pass filtering tends to widen the processed signal. Therefore, if a box-car averaging method is used, the measured duration of the processed signal needs to be decreased by the width of the boxcar used for filtering. Various other low-pass filtering procedures may be used. For a given filter, however, the duration measured generally needs to be adjusted downward by the width of the filter's impulse response.

In general, any filtering performed will be accomplished by an appropriately programmed computer or dedicated hardware designed to perform one or more specific, desired signal processing/filtering functions.

Pacing artifacts can significantly complicate the task of automatically determining electrogram durations, especially for electrode pairs close to the pacing sites. This is because the pacing artifacts are temporally close to the beginning of the electrogram complex. There are several ways to overcome the interference of the pacing artifacts and to simplify the task of determining the beginning of each electrogram complex. In one embodiment, signals recorded while pacing signals are applied and for 1 to 2 milliseconds after the termination of pacing signal application are ignored. Since the pacing artifact is propagated electrically, the pacing artifact is synchronous in all recording channels. Therefore, the most straightforward approach is simply to ignore all signals that are recorded during the pacing. In another embodiment, the effects of pacing artifacts can be reduced or eliminated entirely using either nonlinear or adaptive filtering techniques. These techniques are described in U.S. Pat. No. 5,601,088 which is incorporated in its entirety by reference. In yet another embodiment, response signals from electrodes located near the electrodes used in pacing are ignored. Since response signals from multiple pacing locations are measured, it is possible to ignore some electrode locations near each pacing site. In another embodiment, response signals from electrodes that are used to apply the pacing signals are ignored. If the electrode is connected to the system for recording during pacing, the input amplifiers are saturated during and for some time after the pacing pulse has terminated. The time to recover from saturation varies by recorder system manufacturer and for different models of recorder systems produced by the same manufacturer. Even for systems with fast recovery from saturation, electrograms recorded from pacing electrodes tend to be greatly distorted for 10 ms to 100 ms after pacing due to after-potentials at the electrode-electrolyte interface following pacing. It thus is technically very difficult to obtain an accurate estimate of electrogram duration at a pacing site. In another embodiment, the recorder system is disconnected from all electrodes during the delivery of the pacing signals. For many recorder systems, this would eliminate the pacing artifacts in all recording channels, except for residual artifact signals due to after-potentials which is seen on all channels using the pacing electrode(s).

Once it is determined that a monitoring electrode is located in the reentrant pathway, the tissue near the monitoring electrode is destroyed by creating a lesion having a large surface area and a shallow depth. The tissue may be destroyed (ablated) by heat, chemicals, or other means. To ablate a tissue, an ablation electrode is coupled to a source of ablation energy for transmitting ablation energy at a prescribed power level. To perform an accurate ablation, the location of the ablation electrode and emission of energy must be precisely controlled.

In one embodiment, a multiple electrode ablation catheter described in U.S. Pat. No. 5,582,609, which is incorporated in its entirety by reference, is used to create lesions having a large surface area and a shallow depth. Referring to FIG. 5A, an ablation catheter 100 has a flexible ablating element 102 carried at the distal end and a handle 104 at the proximal end of the catheter 100. The handle 104 and the catheter body 106 carry a steering mechanism 108 for selectively bending or flexing the ablating element 102 in two opposite directions. The flexible ablating element 102 can be configured in various ways to form lesions of different characteristics from long and thin to large and deep in shape. The characteristic of the lesions are controlled by selectively adjusting the size and spacing of energy emitting regions (108 in FIGS. 5B and 5C) along the elements 102, masking the energy emitting regions 108 on the elements to focus ablating energy upon the targeting tissue, altering the electrical connections of wires conveying ablating energy to the energy emitting regions 108 to affect the distribution of ablation energy, altering the shape of the flexible support body to affect the distribution and density of the energy emitting regions 108, and controlling temperature conditions along the energy emitting regions 108 of the elements 102. Larger lesions can be formed by shaping the flexibly body of the catheter 100 as shown in FIGS. 6A and 6B. The energy emitting regions 108 may be continuous or segmented as shown in the drawings. Higher RF power, longer continuous ablation times, and higher ablation set temperatures all cause deeper lesions to be created. Conversely, lower power settings, shorter ablation times, and shorter ablation set temperatures result in more shallow lesions. The relationship of these three ablation parameters and lesion depth varies, depending on the characteristic of the ablation device. Nevertheless, once the effects of these parameters on lesion depth is characterized, ablation can be applied in a prescribed manner to produce the desired lesion depth.

Figure 6:
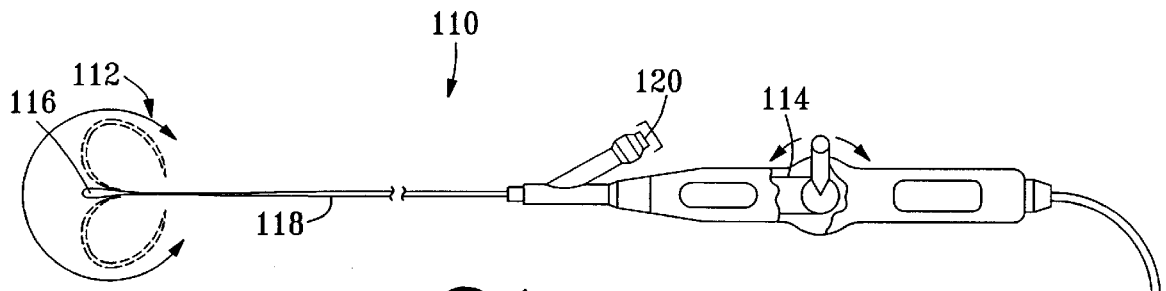
FIG. 6 is a schematic diagram of a balloon ablation catheter.

In another embodiment, a balloon ablation catheter 110 is employed to create a large surface area shallow lesion. Such a catheter is described in pending U.S. patent application Ser. No. 08/010,225 which was filed on Jan. 19, 1996, which description is hereby incorporated by reference. Referring to FIG. 6, the balloon ablation catheter 110 includes an electrode structure 112 at its distal end and a handle 114 at its proximal end. The electrode structure 112 includes an expandable-collapsible body 116. The balloon catheter 110 carries an interior lumen along its length 118. The distal end of the lumen 118 opens into the hollow interior of the expandable-collapsible body 116. The proximal end of the lumen 118 communicates with a port 120 on the handle 114. Once the catheter 110 is introduced into the body in its collapsed form, a liquid inflation medium is conveyed through the port 120 and into the lumen 118 to inflate and maintain the expanded geometry. The expansion in the electrode structure 112 is controlled to create an electrode with a sufficient size to create a lesion having a desired surface area.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method of characterizing heart tissue, comprising:
   recording signals from a surface of the heart during an episode of ventricular tachycardia; and
   determining whether a reentrant pathway lies near the surface of the heart based at least in part on the recorded signals.

2. The method of claim 1 further comprising assessing whether a portion of tissue of the heart is near a slow conduction zone of the reentrant pathway.

3. The method of claim 2 wherein the assessing step comprises entrainment pacing the portion of the heart tissue.

4. The method of claim 3 wherein the step of entrainment pacing comprises:
   applying a pacing signal to the heart tissue; and
   analyzing a post-pacing signal.

5. The method of claim 4 wherein the applying step comprises applying the pacing signal which is in the range of about 1 milliAmpere to about 10 milliAmperes.

6. The method of claim 4 wherein the applying step comprises applying the pacing signal to the heart tissue to stimulate the heart tissue, and wherein the analyzing step comprises analyzing the post-pacing signal to measure a time interval from when the heart tissue is stimulated to a time when a next non-stimulated depolarization of the heart tissue occurs.

7. The method of claim 1 wherein the recording step comprises placing at least one electrode on the surface of the heart to record signals from the surface of the heart.

8. The method of claim 7 wherein the placing step comprises covering the surface of the heart with multiple electrodes.

9. The method of claim 7 wherein the placing step comprises sequentially moving and placing a roving electrode on multiple locations on the surface of the heart.

10. The method of claim 1 wherein the recording step comprises recording signals from an endocardial surface of the heart.

11. The method of claim 1 wherein the determining step comprises evaluating the recorded signals to find diastolic or pre-systolic potentials and using these potentials as the basis for the determining step.

12. A method of ablating heart tissue, comprising:
   recording signals from a surface of the heart during an episode of ventricular tachycardia;
   determining whether a reentrant pathway lies near the surface of the heart based at least in part on the recorded signals;
   assessing whether a portion of tissue of the heart is near a slow conduction zone of the reentrant pathway; and
   ablating the heart tissue to create a shallow lesion if the heart tissue is near the slow conduction zone of the reentrant pathway.

13. The method of claim 12 wherein the ablating step comprises ablating the heart tissue to create the shallow lesion which has a large surface area.

14. The method of claim 12 wherein the ablating step comprises ablating the heart tissue to create the shallow lesion which has a depth in the range of about 3 millimeters to about 4 millimeters.

15. The method of claim 12 wherein the ablating step comprises using a multiple electrode ablation catheter to ablate the heart tissue to create the shallow lesion.

16. The method of claim 12 wherein the ablating step comprises using a balloon ablation catheter to ablate the heart tissue to create the shallow lesion.

17. A system for characterizing heart tissue to identify an ablation site comprising:

an electrode;

a signal generating and recording device electrically coupled with the electrode, the signal generating and recording device configured for receiving signals from a surface of the heart for measuring diastolic and pre-systolic potentials during an episode of ventricular tachycardia when a re-entrant circuit pathway is located near the endocardial tissue of the heart, and further configured for applying a pacing signal to and receiving a post-pacing signal from the heart during an entrainment pacing procedure, the signal generating and recording device comprising a display unit configured for displaying diastolic or pre-systolic potentials during the episode of ventricular tachycardia when a reentrant pathway is located near the endocardial tissue of the heart and displaying a post-pacing signal during the entrainment pacing procedure.

18. The system of claim 17 further comprising a multiple electrode catheter which includes the at least one electrode.

19. The system of claim 18 wherein the multiple electrode catheter is a basket catheter.

20. The system of claim 17 further comprising a roving catheter which includes the at least one electrode.

21. The system of claim 17 wherein the signal generating and recording device includes a computer-controlled electrogram recording and stimulating system capable of controlling pacing pulse parameters, pacing intervals, and a sequence of electrode sites at which pacing signals are applied.

22. A system for ablating heart tissue comprising:

a source of ablation energy;

an ablation catheter which is coupled to the source of ablation energy, includes at least one electrode, and configured to controllably produce a lesion having a large surface area and a shallow depth; and a signal generating and recording device electrically coupled with the at least one electrode, the signal generating and recording device configured for receiving signals from a surface of the heart and measuring diastolic and pre-systolic potentials during an episode of ventricular tachycardia when a re-entrant circuit pathway is located near the endocardial tissue of the heart, and for applying a pacing signal to and receiving a post-pacing signal from the heart during an entrainment pacing procedure, the signal generating and recording device comprising a display unit configured for displaying diastolic or pre-systolic potentials during the episode of ventricular tachycardia when a reentrant pathway is located near the endocardial tissue of the heart and displaying a post-pacing signal during the entrainment pacing procedure.

23. The system of claim 22 wherein the ablation catheter is a balloon ablation catheter.

24. The system of claim 22 wherein the ablation catheter is a multiple electrode ablation catheter.

25. The system of claim 22 wherein the source of ablation energy is a radio frequency generator.

* * * * *